(12) United States Patent
Ham et al.

(10) Patent No.: US 6,989,458 B2
(45) Date of Patent: Jan. 24, 2006

(54) PROCESS FOR PREPARING PROSTAGLANDIN DERIVATIVES AND STEREOSPECIFIC STARTING MATERIAL THEREOF

(75) Inventors: Won-Hun Ham, Seoul (KR); Chang-Young Oh, Seoul (KR); Yong-Hyun Kim, Seoul (KR); Yiu-Suk Lee, Seoul (KR); Kee-Young Lee, Seoul (KR)

(73) Assignee: Yonsung Fine Chemical Co., (KR)

( * ) Notice: Subject to any disclaimer, the term of this patent is extended or adjusted under 35 U.S.C. 154(b) by 0 days.

(21) Appl. No.: 11/021,284

(22) Filed: Dec. 22, 2004

(65) Prior Publication Data
US 2005/0192451 A1 Sep. 1, 2005

Related U.S. Application Data

(60) Division of application No. 10/476,115, filed on Oct. 24, 2003, now Pat. No. 6,852,880, which is a continuation of application No. PCT/KR02/00845, filed on May 7, 2002.

(30) Foreign Application Priority Data
May 8, 2001 (KR) ............................. 2001-25011

(51) Int. Cl.
*C07F 7/04* (2006.01)
*C07C 67/02* (2006.01)

(52) U.S. Cl. .................................... 556/485; 560/254
(58) Field of Classification Search ............... 556/485; 560/254
See application file for complete search history.

(56) References Cited

U.S. PATENT DOCUMENTS

| 4,963,492 | A | * | 10/1990 | Keller et al. .............. 435/280 |
| 5,607,978 | A | | 3/1997 | Woodward et al. |
| 6,124,344 | A | | 9/2000 | Burk |
| 6,388,128 | B1 | * | 5/2002 | Conrow .................... 562/503 |
| 6,689,901 | B2 | | 2/2004 | Henegar |
| 6,852,880 | B2 | * | 2/2005 | Ham et al. ................. 562/465 |

FOREIGN PATENT DOCUMENTS

EP 0364417 A1 4/1990
WO WO-95/11003 4/1995

OTHER PUBLICATIONS

Yu, Ming et al., DN 137:93381 HCAPLUS, abstract of Journal of Organic Chemistry (2002), 67(13), 4553-4558.*

* cited by examiner

*Primary Examiner*—Sabiha Qazi
(74) *Attorney, Agent, or Firm*—Peter F. Corless; Christine C. O'Day; Edwards & Angell, LLP

(57) ABSTRACT

The present invention relates to a process for effectively preparing prostaglanin derivatives and to a stereospecific alkyl halide containing 15S-alcohol group as a starting material.

1 Claim, No Drawings

PROCESS FOR PREPARING PROSTAGLANDIN DERIVATIVES AND STEREOSPECIFIC STARTING MATERIAL THEREOF

This application is a division of U.S. patent application Ser. No. 10/476,115, filed Oct. 24, 2003, now U.S. Pat. No. 6,852,880, which was a continuation of International Application No. PCT/KR02/00845, filed May 7, 2002.

TECHNICAL FIELD

The present invention relates to a novel process for preparing a prostaglandin derivative of the following formula (1):

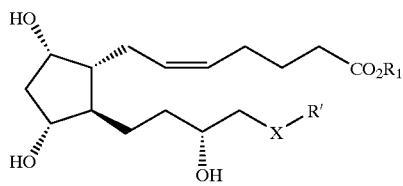

in which $R_1$ represents H or $C_1$–$C_5$-alkyl,

X represents $CH_2$, O, or S, and

R' represents $C_2$–$C_4$-alkyl; phenyl optionally substituted by halogen, $C_1$–$C_5$-alkyl, $C_1$–$C_4$-alkoxy, $CF_3$, or $C_1$–$C_3$-aliphatic acylamino; 5- or 6-membered heterocycle containing one or more hetero atoms selected from a group consisting of nitrogen, oxygen and sulfur; $C_3$–$C_7$-cycloalkyl; or $C_3$–$C_7$-cycloalkenyl, a 13,14-dihydro-PGF$_{2\alpha}$ ester derivative, and to an alkyl halide of the following formula (3a):

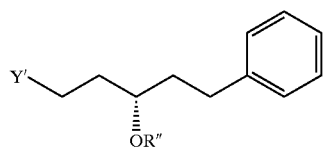

in which

Y' represents Br or I, and

R" represents a hydroxy-protecting group, preferably trimethylsilyl, triethylsilyl, t-butyldimethylsilyl, t-butyldiphenylsilyl, phenyldimethylsilyl, or tetrahydrofuranyl, as a starting material.

BACKGROUND ART

Prostaglandin derivative of the above formula (1) is known in *Drugs of the Future*, 1992, 17(8), 691–704; *J Med Chern.*, 1993, 36, 243–248, etc. and a process of the following Reaction Scheme 1 published in WO 93/00329 can be mentioned as the typical synthesis thereof.

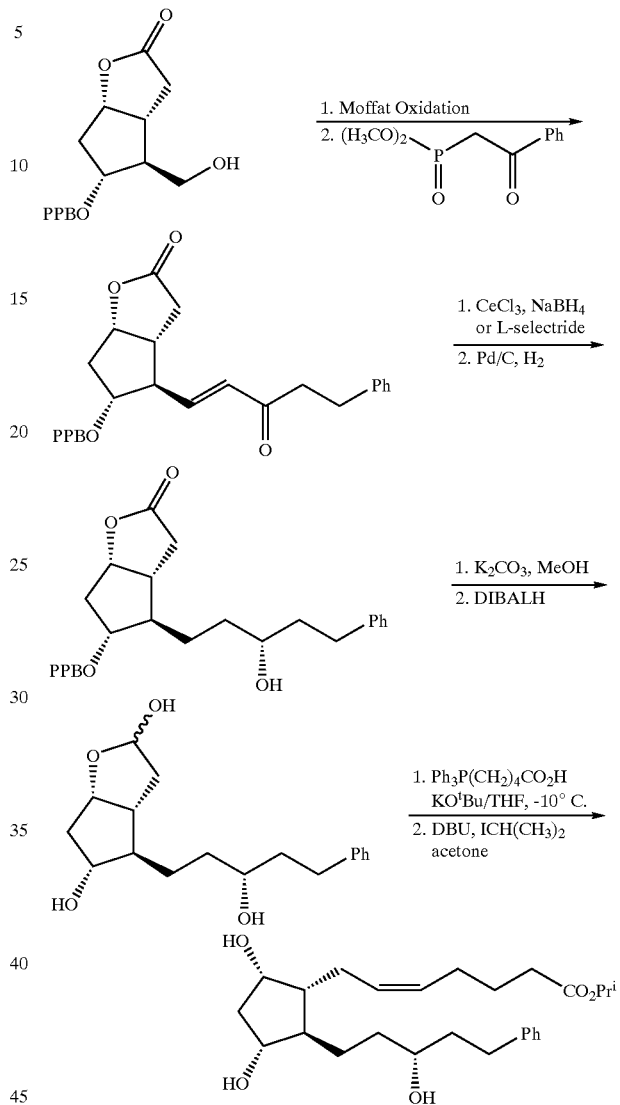

In the above process, ω-chain is introduced into the starting material of Corey lactone by Wadworth-Emmons method, the ketone group at C15 position is reduced to an alcohol group, the remained double bond is reduced again using Pd, α-chain is introduced into a lactol as obtained through some consecutive reactions by Wittig reaction, and the terminal group is esterified.

However, the above process has been identified to have the following problems.

First, the diastereomeric mixture resulted from the introduction of ω-chain and reduction of the ketone group at C15 position comprises 15S-isomer and 15R-isomer in a ratio of 7:3. Therefore, stereoselectivity of the process is not satisfactory. Further, since these isomers can hardly be separated, the yield of the desired 15S-isomer is as very low as 38%.

Second, the yield of the esterification reaction of the terminal carboxylic acid after introduction of α-chain by Wittig reaction is reported to be less than 40%. This is the final step of the process, and so the low yield of the final step reaction may exert fatal and serious influence on the total efficacy of the synthesis.

Third, Corey lactone used as a starting material is very expensive, which makes the total process uneconomic.

DISCLOSURE OF INVENTION

Thus, the present inventors have extensively studied to develop an economic and effective process for preparing the compound of formula (1) by solving the problems of prior arts as explained above. As a result, we newly designed an alkyl halide containing 15S-alcohol group and then completed a process for preparing the compound of formula (1), starting from 1,4-addition reaction at the α,β-unsaturated ketone group. According to the process of the present invention, the yield may be increased by using a stereospecific starting material instead of reducing the C15 ketone in a poor stereoselective manner; particularly, the low efficacy due to the low yield of esterification reaction of the terminal carboxylic acid may be improved; and there is no more need to use the expensive Corey lactone as a starting material. Therefore, the present invention provides an economic and effective synthetic process that is suitable for a mass production.

Therefore, an object of the present invention is to provide a process for preparing a prostaglandin derivative of formula (1).

It is another object of the present invention to provide an alkyl halide of formula (3a) as an effective starting material.

BEST MODE FOR CARRYING OUT THE INVENTION

The present invention relates to a process for preparing a compound of the following formula (1):

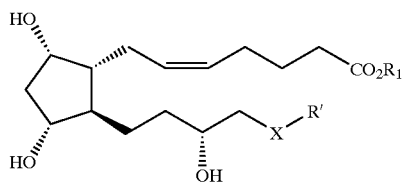

in which
$R_1$ represents H or $C_1$–$C_5$-alkyl,
X represents $CH_2$, O, or S, and
R' represents $C_2$–$C_4$-alkyl; phenyl optionally substituted by halogen, $C_1$–$C_5$-alkyl, $C_1$–$C_4$-alkoxy, $CF_3$, $C_1$–$C_3$-aliphatic acylamino; 5- or 6-membered heterocycle containing one or more hetero atoms selected from a group consisting of nitrogen, oxygen and sulfur; $C_3$–$C_7$-cycloalkyl; or $C_3$–$C_7$-cycloalkenyl, which comprises the first step wherein an alkyl halide containing 15S-alcohol of the following formula (3):

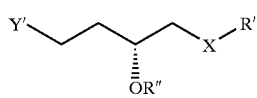

in which
X and R' are defined as above,
Y represents a leaving group, preferably halogen, and
R" represents a hydroxy-protecting group, preferably trimethylsilyl, triethylsilyl, t-butyldimethylsilyl, t-butyldiphenylsilyl, phenyldimethylsilyl, or tetrahydrofuranyl, is converted into a cuprate thereof and the cuprate compound is subjected to a stereoselective 1,4-addition reaction to an α,β-unsaturated ketone compound of the following formula (2):

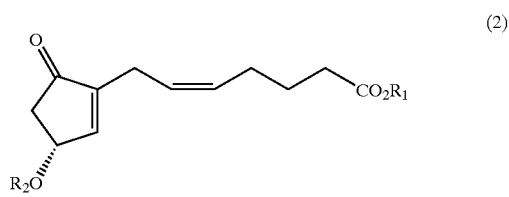

in which
$R_1$ is defined as above, and
$R_2$ represents a hydroxy-protecting group, preferably trimethylsilyl, triethylsilyl, t-butyldimethylsilyl, t-butyldiphenylsilyl, phenyldimethylsilyl, or tetrahydrofuranyl, to give a compound of the following formula (4):

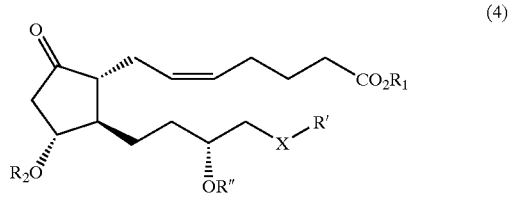

in which X, R', R", $R_1$ and $R_2$ are defined as above; the second step wherein the ketone group on the cyclopentanone ring of the compound of formula (4) is reduced using a metal hydride to give an α-alcohol compound of the following formula (5):

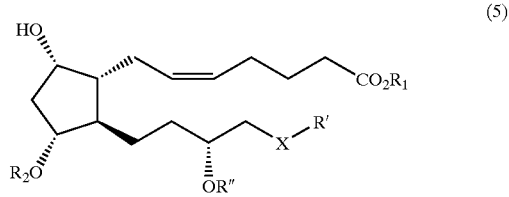

in which X R', R", $R_1$ and $R_2$ are defined as above; and the third step wherein the alcohol protecting groups on the cyclopentanone ring and a ω-chain in the compound of formula (5) are removed to give the compound of formula (1).

The process according to the present invention is depicted in the following Reaction Scheme 2 below.

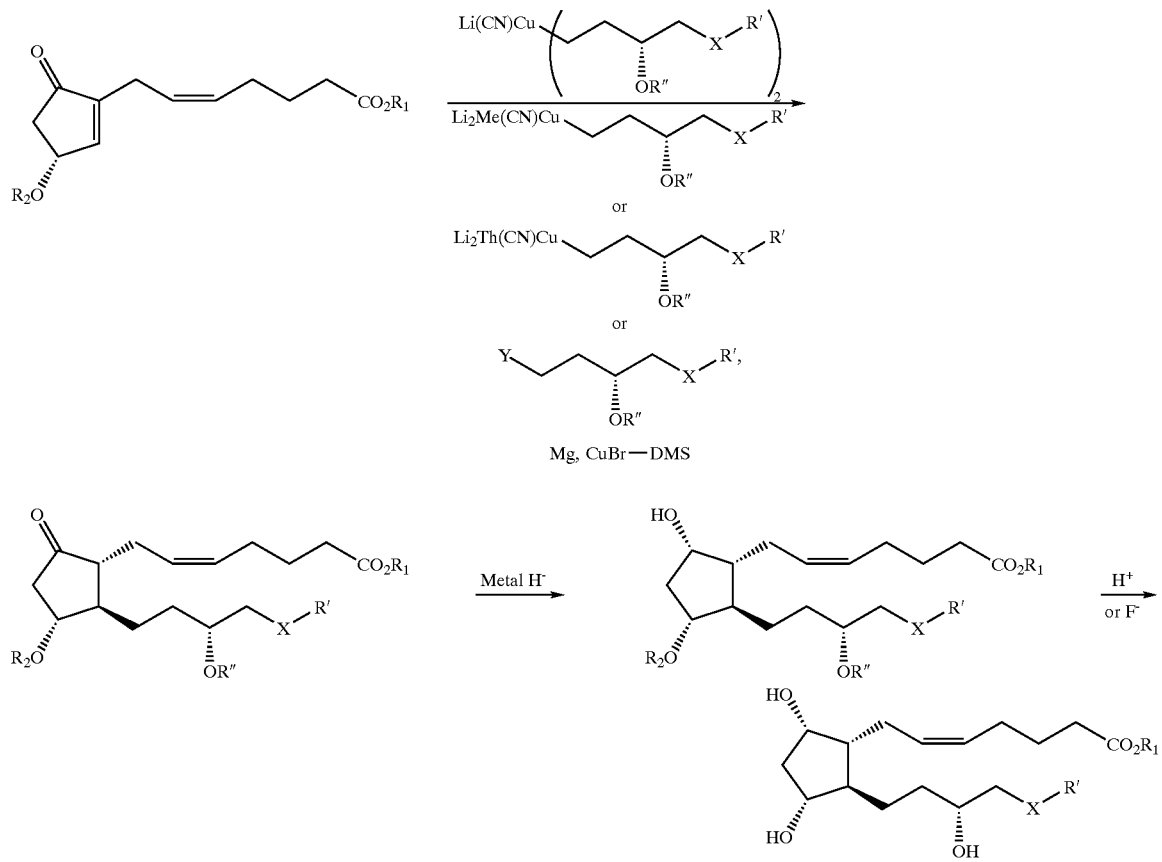

The process of the present invention proceeds through three steps, each of which is specifically explained in the following.

The First Step: Preparation of the Compound of Formula (4) from the Compounds of Formulae (2) and (3)

The cuprate compound that is formed from the alkyl halide of formula (3) by various methods as explained below is subjected to 1,4-addition reaction to the α,β-unsaturated ketone group of the compound of formula (2) to give the compound of formula (4). Here, the cuprate compound is introduced into the opposite side to the alkoxy group on the cyclopentenone due to the steric hindrance of the alkoxy group, resulting in a trans configuration with respect to the alkoxy group. The ω-chain thus introduced causes another steric hindrance to the α-chain of the cyclopentenone, whereby the compound of formula (4) in which α-chain and ω-chain have a trans configuration to each other is obtained.

The cuprate compound can be obtained from the compound of formula (3) by i) adding t-BuLi and then adding one substance selected from a group consisting of CuCN, (2-thienyl)Cu(CN)Li and MeCu(CN)Li to the compound of formula (3); or ii) adding one substance selected from a group consisting of CuBr.DMS, CuI and CuBr to a Grignard reagent that is formed from magnesium and the compound of formula (3).

Below, the process for preparing the compound of formula (4) from the alkyl halide of formula (3), where the cuprate compound acts as an intermediate, is specifically explained.

Method ⓐ

To 2 equivalents of the compound of formula (3) dissolved in a solvent is added 4 equivalents of t-BuLi at −78° C., which is then stirred. 1 equivalent of CuCN is added thereto. The temperature of the reaction solution is raised to −10° C. to give a lower order-cuprate in a homogeneous state. This cuprate is cooled again to −78° C. and then reacted with 0.8–1.0 equivalent of the compound of formula (2).

Method ⓑ

To 1 equivalent of the compound of formula (3) dissolved in a solvent is added 2 equivalents of t-BuLi at −78° C., which is then stirred. 1 equivalent of (2-thienyl)Cu(CN)Li or MeCu(CN)Li is added thereto. The temperature of the reaction solution is slowly raised to −40° C. over 30 minutes and then lowered again to −78° C. to give a higher order-cuprate. This cuprate is reacted with 0.8–1.0 equivalent of the compound of formula (2).

Method ⓒ

To 1 equivalent of the compound of formula (3) dissolved in a solvent is added 3–4 equivalents of Mg. The Grignard solution thus obtained is cooled to −78° C., and 0.3–1 equivalent of a substance selected from a group consisting of CuBr.DMS, CuI, and CuBr is added. The reaction mixture is stirred for 1 hour to give Normant reagent. This reagent is reacted with 0.8–1.0 equivalent of the compound of formula (2).

The compound of formula (3) used as a starting material in the above may be obtained by a process as exemplified in the following Reaction Scheme 3.

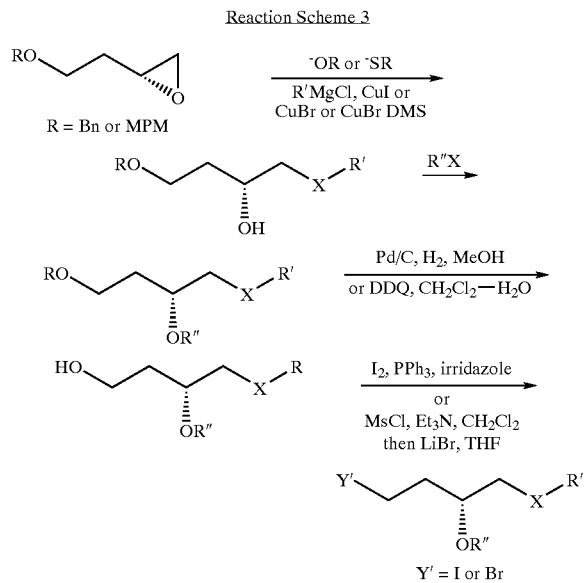

That is, a nucleophile, preferably carbanion, phenol, thiophenol, or alkaline salt of phenol or thiophenol, is reacted with a chiral epoxide that can be prepared by a process known in J. Chem. Research(S), 1983, 10–11 to open the ring in a stereospecific manner to give an alcohol compound having S stereochemistry. Particularly, in the case of carbanion, the alcohol compound can be obtained by adding 1~2 equivalents of a Grignard reagent and a catalytic amount (0.05~0.5 equivalent) of a substance selected from a group consisting of CuI, CuBr, and CuBr.DMS, stirring for 10 minutes, and slowly adding dropwise an epoxide in a solvent selected from a group consisting of diethylether, tetrahydrofuran and dimethylsulfide at reaction temperatures of −20~20° C.

Then, the alcohol is protected by a hydroxy-protecting group, preferably triethylsilyl, t-butyldimethylsilyl, t-butyldiphenylsilyl, phenyldimethylsilyl, or tetrahydrofuranyl, and the protecting group of the primary alcohol is removed. Particularly, the benzyl group used as a protecting group can be removed by a catalytic hydrogenation reaction in a solvent selected from a group consisting of methanol and ethanol, and in the presence of palladium as a catalyst; and the paramethoxybenzyl group can be removed in a solvent mixture of dichloromethane and water in the presence of DDQ (2,3-dichloro-5,6-dicyano-1,4-benzoquinone)(1.0~2.0 equivalent) at room temperature.

Finally, the primary alcohol is iodinated by $I_2$, $PPh_3$, and imidazole in a solvent mixture of acetonitrile and diethylether; or brominated by $CBr_4$ and $PPh_3$, or reacting with methane sulfonyl chloride and triethylamine to give a methanesulfonate, which is then reacted with LiBr in THF solvent.

Particularly, a compound of the following formula (3a) among the compound of formula (3):

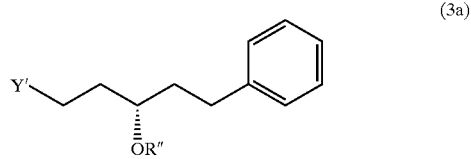

in which Y' represents Br or I, and R" represents a hydroxy-protecting group, is novel, and thus, it is another object of the present invention to provide the novel compound of formula (3a).

The compound of formula (2) can be prepared according to a process described in J Org. Chem., 1978, 43, 1641–1643, and (2-thienyl)Cu(CN)Li or MeCu(CN)Li can be obtained by adding the commercially available 2-thienyl lithium or MeLi to CuCN.

In the above reaction, the solvent dissolving the compounds of formulae (2) and (3) is selected from a group consisting of tetrahydrofuran and diethylether, and the solvent dissolving t-BuLi is n-pentane. After the completion of each reaction, an aqueous solution of $NH_4Cl/NH_4OH$ (9/1) is added to stop the reaction, Then, the reaction solution is extracted with diethylether, concentrated, and purified by column chromatography.

The Second Step: Preparation of the Compound of Formula (5) by Reduction of the Compound of Formula (4)

The compound of formula (4) obtained by the above 1,4-addition reaction has a ketone group, which can be reduced by various metal hydrides. As the metal hydrides that can be used, those having a heavy steric hindrance, preferably those selected from a group consisting of sodiumborohydride ($NaBH_4$), L-selectride, N-selectride and K-selectride, and particularly preferably L-selectride can be mentioned. This is because the hydride is apt to attack the cyclopentanone ring from the opposite direction with respect to the alkoxy group in the compound of formula (4) due to the steric hindrance of the alkoxy group, as the metal hydride is bulkier, to selectively give the desired α-alcohol. The reaction is carried out by adding 1~3 equivalents of L-selectride to 1 equivalent of the compound of formula (4) dissolved in a solvent at −78° C., stirring for 1 to 2 hours, and adding 30% $H_2O_2$ to stop the reaction. The reaction solution is stirred for 30 minutes at 0° C., extracted with diethylether, and concentrated to give the compound of formula (5) in a stereoselective manner. This compound is used in the next reaction without further purification. The solvent used in the above reaction is selected from a group consisting of tetrahydrofuran, diethylether and dichloromethane.

The Third Step: Preparation of the Compound of Formula (1) Through Deprotection of the Compound of Formula (5)

The two alcohol protecting groups in the compound of formula (5) can be removed under an acidic condition, or by using various fluorides (F) particularly when the protecting group is silyl. More specifically, the following methods can be exemplified.

Method Using an Acidic Condition

Method ⓐ

Deprotection is achieved by stirring for 24~48 hours at room temperature in the presence of excess $NaHSO_4$ in a solvent mixture of tetrahydrofuran and water (2:1).

Method Using Fluorides

Deprotection is achieved by stirring for 4 hours at 0° C.~room temperature in the presence of 2~4 equivalents of tetrabutylammonium fluoride ($Bu_4N^+F^-$) in a solvent of tetrahydrofuran (Method ⓑ); or reacting for 3~4 hours at 0° C. with 2~10 equivalents of hydrogen fluoride pyridine (HF-pyridine) in a solvent of dichloromethane (Method ⓒ); or reacting for 4 hours with fluorosilicic acid ($H_2SiF_6$) in a solvent of acetonitrile according to DeShong method(*J Org. Chem.*, 1992, 57, 2492) (Method ⓓ).

The present invention will be more specifically explained in the following examples. However, it should be understood that the following examples are intended to illustrate the present invention but not in any manner to limit the scope of the present invention.

EXAMPLE 1

Preparation of the Compound of Formula (3)

Preparation of 1-(4-methoxy-benzyloxy)-5-phenyl-pentan-3-ol

Benzyl magnesium chloride (2.0M in THF) (64.6 ml, 129.2 mmol) was added to THF (77 ml) and cooled to 0° C. CuI (1.9 g, 9.94 mmol) was added, and the mixture was stirred for 10 minutes. 2-[2-(4-Methoxy-benzyloxy)-ethyl]-oxirane (19.5 g, 99.4 mmol) dissolved in THF (120 ml) was slowly added dropwise thereto. The reaction mixture was stirred for 1 hour at room temperature and saturated aqueous $NH_4Cl$ solution (100 ml) was added to separate the organic layer. The aqueous layer was extracted with diethylether (100 ml×2). The organic layers were combined, washed with saturated aqueous NaCl solution, dried over $MgSO_4$, filtered, and concentrated to give 1-(4-methoxy-benzyloxy)-5-phenyl-pentan-(S)-3-ol (30 g) of a pale yellow oil. This compound was used in the next reaction without further purification.

Preparation of (S)-3-(t-butyldimethylsilyloxy)-5-(4-methoxy-benzyloxy)-1-phenyl Pentane To DMF (390 ml) were added 1-(4-methoxy-benzyloxy)-5-phenyl-pentan-(S)-3-ol (30 g unpurified), imidazole (20.3 g, 298.2 mmol) and TBDMSCl (23 g, 149.8 mmol) in the order, and the resulting mixture was stirred for 12 hours at room temperature. After completion of reaction, the reaction mixture was diluted with water (500 ml) and extracted with ethyl acetate (100 ml×3). The organic layers were combined, washed with saturated aqueous NaCl solution, dried over $MgSO_4$, filtered, and concentrated. The residue was purified by silica gel column chromatography (hexane:ethyl acetate=20:1) to give (S)-3-(t-butyldimethylsilyloxy)-5-(4-methoxy-benzyloxy)-1-phenyl pentane (35 g, Yield of 2 steps 85%) of a colorless and transparent oil.

Preparation of (S)-3-(t-butyldimethylsilyloxy)-5-phenyl-pentan-1-ol (S)-3-(t-butyldimethylsilyloxy)-5-(4-methoxy-benzyloxy)-1-phenyl pentane (15 g, 36.2 mmol) was dissolved in a solvent mixture of dichloromethane-water (20:1) (252 ml) DDQ (8.2 g, 36.2 mmol) was added thereto and the mixture was stirred for 30 minutes at room temperature. After completion of the reaction, saturated aqueous $NaHCO_3$ solution (100 ml) was added to the reaction solution to stop the reaction. The organic layer was separated and the aqueous layer was extracted with dichloromethane. The organic layers were combined, washed with saturated aqueous $NaHCO_3$ solution and saturated aqueous NaCl solution, dried over $MgSO_4$, filtered, and concentrated. The residue was purified by silica gel column chromatography (hexane:ethyl acetate=15:1) to give (S)-3-(t-butyldimethylsilyloxy)-5-phenyl-pentan-1-ol (10.6 g, Yield 99%) of a yellow oil.

Preparation of (S)-3-(t-butyldimethylsilyloxy)-5-bromo-1-phenyl pentane (S)-3-(t-butyldimethylsilyloxy)-5-phenyl-pentan-1-ol (10.6 g, 36 mmol) was dissolved in dichloromethane (80 ml), triethylamine (12.6 ml, 90.5 mmol) was added, and the mixture was cooled to 0° C. Methane sulfonyl chloride (4.2 ml, 54.3 mmol) was slowly added dropwise and the resulting mixture was stirred for 12 hours. After completion of the reaction, the reaction mixture was diluted with water (50 ml). The organic layer was separated and the aqueous layer was extracted with dichloromethane (50 ml×2). The organic layers were combined, washed with saturated aqueous NaCl solution, dried over $MgSO_4$, filtered, and concentrated. Without further purification, the residue was dissolved in THF (60 ml). LiBr (7.86 g, 90.5 mmol) was added thereto and the mixture was refluxed for 4 hours. After completion of the reaction, water (80 ml) was added to the reaction solution which was then extracted with diethylether. The organic layers were combined, washed with saturated aqueous NaCl solution, dried over $MgSO_4$, filtered, and concentrated. The residue was purified by silica gel column chromatography (hexane:ethyl acetate=20:1) to give colorless and transparent (S)-3-(t-butyldimethylsilyloxy)5-bromo-1-phenyl pentane (11 g, Yield 86%).

EXAMPLE 2

Preparation of the Compound of Formula (4) According to Method ⓐ

(S)-3-(t-butyldimethylsilyloxy)-5-bromo-1-phenyl pentane (8 mmol) was dissolved in diethylether (17 ml) and cooled to −78° C. t-BuLi (1.7M pentane solution, 16 mmol) was slowly added dropwise thereto and the mixture was stirred for 20 minutes. Then, CuCN (4 mmol) was added and the temperature of the reaction solution was slowly raised to −10° C. to make the solution homogeneous. The reaction solution was cooled again to −78° C. 7-[(R)-3-(t-butyldimethylsilyloxy)-5-oxo-cyclopent-1-enyl]-hept-5-enoic acid isopropyl ester (3.25 mmol) dissolved in $Et_2O$ (2.5 ml) was slowly added dropwise and the mixture was stirred for 2 hours. The temperature of the reaction solution was raised to −30° C., the reaction was stopped by the addition of 20 ml of saturated aqueous $NH_4Cl$ solution/28% aqueous $NH_4OH$ solution (9/1), and the reaction solution was warmed to room temperature. The reaction solution was diluted with diethylether, washed with water and brine, dried over $Na_2SO_4$, filtered, and concentrated under vacuum. The residue was purified by silica gel column chromatography (hexane:ethyl acetate=20:1) to give 11,15-O-bis(t-butyldimethylsilyl)-13,14-dihydro-17-phenyl $PGE_{2\alpha}$ isopropyl ester in a yield of 82%.

EXAMPLE 3

Preparation of the Compound of Formula (4) According to Method ⓑ

(S)-3-(t-butyldimethylsilyloxy)-5-bromo-1-phenyl pentane (3.5 mmol) was dissolved in diethylether (30 ml) and cooled to −78° C. t-BuLi (1.7M pentane solution, 7.35 mmol) was added dropwise and the mixture was stirred for 10 minutes. (2-Thienyl)Cu(CN)Li (0.25M THF solution, 3 mmol) which was newly prepared in another flask was added dropwise thereto. The reaction solution was slowly warmed to −40° C. over 30 minutes and then cooled to −78° C. 7-[(R)-3-(t-butyldimethylsilyl oxy)-5-oxo-cyclopent-1-enyl]-hept-5-enoic acid isopropyl ester (2.7 mmol) dissolved in diethylether (15 ml) was slowly added dropwise thereto. Immediately after the dropwise addition, the reaction vessel was transferred to a cryostat of −45° C., and then the reaction solution was warmed to −30° C. over 30 minutes. After completion of the reaction, the reaction was stopped by adding 10 ml of aqueous $NH_4Cl/NH_4OH(9/1)$ solution. The reaction solution was warmed to room temperature, diluted with diethylether, washed with water and brine, dried over $Na_2SO_4$, filtered, and concentrated under vacuum. The residue was purified by silica gel column chromatography (hexane:ethyl acetate=20:1) to give 11,15-O-bis(t-butyldimethylsilyl)-13,14-dihydro-17-phenyl $PGE_{2\alpha}$ isopropyl ester in a yield of 83%.

EXAMPLE 4

Preparation of the Compound of Formula (4) According to Method ⓒ

To a flask containing magnesium turning (25 mmol) was introduced a solution wherein (S)-3-(t-butyldimethylsilyloxy)-5-bromo-1-phenyl pentane (8.3 mmol) and 1,2-dibromoethane (0.05 ml) were dissolved in THF (1.6 ml). The reaction solution was warmed in a thermostat of 70° C. to initiate formation of Grignard reagent, cooled again to room temperature, and stirred for 30 minutes. This solution was diluted with THF (5 ml), stirred for further 1.25 hour, and cooled to −78° C. CuBr(DMS) (2.0 mmol) dissolved in dimethylsulfide (4 ml) was added dropwise and the mixture was stirred for 1 hour. 7-[(R)-3-(t-butyldimethylsilyloxy)-5-oxo-cyclopent-1-enyl]-hept-5-enoic acid isopropyl ester (6.8 mmol) dissolved in diethylether (7 ml) was slowly added dropwise thereto and the mixture was stirred for 1 hour. After completion of the reaction, the reaction solution was warmed to −30° C. The reaction was stopped by the addition of 20 ml of aqueous $NH_4Cl/NH_4OH(9/1)$ solution, which was then warmed to room temperature. The reaction solution was diluted with diethylether, washed with water and brine, dried over $Na_2SO_4$, filtered, and concentrated under vacuum. The residue was purified by silica gel column chromatography (hexane:ethyl acetate=20:1) to give 11,15-O-bis(t-butyldimethylsilyl)-13,14-dihydro-17-phenyl $PGE_{2\alpha}$ isopropyl ester in a yield of 77%.

EXAMPLE 5

Preparation of the Compound of Formula (5)

11,15-O-bis(t-butyldimethylsilyl)-13,14-dihydro-17-phenyl $PGE_{2\alpha}$ isopropyl ester (3.67 mmol) was dissolved in THF (40 ml), the reaction solution was cooled to −78° C., and L-selectride (1M THF solution, 7.35 mmol) was slowly added dropwise thereto. At this temperature the reaction solution was stirred for 2 hours and the reaction was stopped by the addition of hydrogen peroxide (30% aqueous solution, 16 mmol). The reaction solution was stirred for 30 minutes at 0° C. and extracted with diethylether. The organic layers were combined, washed with water and brine, dried over magnesium sulfate, filtered, and concentrated under vacuum. The residue was purified by silica gel column chromatography (hexane:ethyl acetate=10:1) to give 11,15-O-bis(t-butyldimethylsilyl)-13,14-dihydro-17-phenyl $PGF_{2\alpha}$ isopropyl ester in the yield of 90%.

EXAMPLE 6

Preparation of the Compound of Formula (1) According to Method ⓐ

11,15-O-bis(t-butyldimethylsilyl)-13,14 dihydro-17-phenyl $PGF_{2\alpha}$ isopropyl ester (4.32 mmol) was dissolved in THF (25 ml), $NaHSO_4.H_2O$ (17.3 mmol) dissolved in water (12.5 ml) was added thereto, and the mixture was stirred for 24 hours at room temperature. After completion of the reaction, the reaction solution was extracted with water (20 ml) and $CH_2Cl_2$ (85 ml). The organic layers were combined, washed with saturated aqueous $NaHCO_3$ solution, dried over magnesium sulfate, filtered, and concentrated. The residue was purified by silica gel column chromatography (hexane:ethyl acetate=1:3) to give 13,14-dihydro-17-phenyl $PGF_{2\alpha}$ isopropyl ester in a yield of 75%.

EXAMPLE 7

Preparation of the Compound of Formula (1) According to Method ⓒ

11,15-O-bis(t-butyldimethylsilyl)-13,14-dihydro-17-phenyl $PGF_{2\alpha}$ isopropyl ester (1.22 mmol) was dissolved in dichloromethane (25 ml), HF.pyr (2.5 ml) was added thereto at 0° C., and the mixture was stirred for 3 hours. After completion of the reaction, the reaction solution was diluted with dichloromethane (10 ml), which was then poured into saturated aqueous $NaHCO_3$ solution of 0° C. The organic layer was separated and the aqueous layer was extracted with dichloromethane. The organic layers were combined, dried over magnesium sulfate, filtered, and concentrated. The residue was purified by silica gel column chromatography (hexane:ethyl acetate=1:3) to give 13,14-dihydro-17-phenyl $PGF_{2\alpha}$ isopropyl ester in the yield of 82%.

EXAMPLE 8

Preparation of the Compound of Formula (1) According to Method ⓓ

11,15-O-bis(t-butyldimethylsilyl)-13,14-dihydro-17-phenyl $PGF_{2\alpha}$ isopropyl ester (3.6 mmol) was dissolved in acetonitrile (15 ml), $H_2SiF_6$ (4 ml, 25% wt aqueous solution) was added dropwise thereto in an ice bath, and the mixture was warmed to room temperature and stirred for 4 hours. After completion of the reaction, saturated aqueous $NaHCO_3$ solution was added thereto. The aqueous layer was extracted with dichloromethane. The organic layers were combined, washed with water and brine, dried over magnesium sulfate, filtered, and concentrated. The residue was purified by silica gel column chromatography (hexane:ethyl acetate=1:3) to give 13,14-dihydro-17-phenyl $PGF_{2\alpha}$ isopropyl ester in the yield of 95%.

INDUSTRIAL APPLICABILITY

In the process of the present invention, a stereospecific starting material is used instead of reducing the ω-chain that may generate undesirable isomers and result in a yield decrease. Further, esterification of the carboxylic acid in the unstable prostaglandin compound in the final step can be avoided, which in turn results in a yield increase in a considerable degree. That is, the total yield of the process according to the present invention is 38 to 51% based on the yields of examples above, which is much higher than the maximum yield of 15% of the previous process. Moreover, according to the present invention, the 15R-isomer resulted from the reduction of ω-chain as an impurity, which can hardly be removed, is not generated, and also the production of impurity from the esterification reaction can be prevented. As a result, the prostaglandin derivative of formula (1) can be easily purified, and so can be synthesized in an economic and effective manner.

What is claimed is:

1. A compound of the following formula (3a):

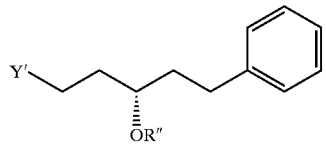

(3a)

in which
Y' represents Br or I, and
R'' represents a hydroxy-protecting group.

* * * * *